US00PP16569P2

(12) United States Plant Patent
Stemkens

(10) Patent No.: US PP16,569 P2
(45) Date of Patent: May 23, 2006

(54) ***NEMESIA* PLANT NAMED 'NEMHSWHI'**

(50) Latin Name: ***Nemesia* hybrid**
Varietal Denomination: Nemhswhi

(75) Inventor: Henricus G. W. Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 205 days.

(21) Appl. No.: 11/005,103

(22) Filed: Dec. 6, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
(74) *Attorney, Agent, or Firm*—Edouard G. Lebel

(57) ABSTRACT

A new and distinct cultivar of *Nemesia* plant named 'Nemhswhi' that is characterized by a semi-trailing and compact habit, white flowers, a yellow palate, very early flowering and absolutely no seedset. In combination these characteristics set 'Nemhswhi' apart from all other existing varieties of *Nemesia* known to the inventor.

1 Drawing Sheet

Latin name of the genus and species of the plant claimed: *Nemesia* hybrid.
Varietal denomination: 'Nemhswhi'.

BACKGROUND OF THE NEW PLANT

The present invention comprises a new and distinct cultivar of *Nemesia* plant, botanically known as *Nemesia* hybrida, and hereinafter referred to by the cultivar name 'Nemhswhi.'

The new *Nemesia* is a product of a planned breeding program conducted by the inventor in Enkhuizen, The Netherlands. The goals of the breeding program were to improve on plant habit by breeding plants that were more compact and basal branching. Earliness of flowering was another character that was very important in the breeding process, together with producing no seed-pods.

The new *Nemesia* originated from a cross-pollination made by the inventor in 2000 of an unpatented *Nemesia* plant, named 'A233-1', as the female, or seed, parent with an unpatented *Nemesia* plant named 'A71-2', as the male, or pollen, parent. The cultivar 'Nemhswhi' was discovered and selected by the inventor as a plant within the progeny from this cross-pollination in a controlled environment in Enkhuizen, The Netherlands, in 2001.

As a result of this cross the present cultivar was created in 2001 in Enkhuizen, Netherlands and has been repeatedly asexually reproduced by cuttings in Enkhuizen, Netherlands and Sarrians, France over a two-year period. It has been found to retain its distinctive characteristics through successive propagations, and this novelty appears to be firmly fixed.

DESCRIPTION OF THE DRAWING

This new *Nemesia* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Nemesia*. The data that define these characteristics were collected from asexual reproductions carried out in Enkhuizen, Netherlands. The plant history was taken on 14 weeks old plants, blossomed under natural light in a greenhouse and grown in a 10.5 cm container. Colour readings were taken in the greenhouse under ambient light. Colour references are primarily to The R.H.S. Colour Chart of The Royal Horticultural Society of London.

TABLE 1

Differences between the new cultivar 'Nemhswhi', its parents and a similar cultivar

| | 'Nemhswhi' | 'A233-1' | 'A71-2' | 'Pensug' |
|---|---|---|---|---|
| Seedset | No | Little | Plentiful | Plentiful |
| Flower size | Medium | Medium | Small | Small |
| Flower color | White | White | White | White |
| Palate color | Yellow | Yellow | White | Yellow |

The commercial name of the most resembling variety is 'Vanilla Schet.' This has been the synonym in Europe of 'Sugar Girl.' The patented name of this variety if 'Pensug' and its U.S. Plant Pat. No. is 12,811.

The plant:

*Classification.*—Botanical: *Nemesia*. Species: *Hybrida.*

*Parentage.*—Female parent: A seedling named 'A233-1' is one of our seedlings from our A-generation of plants bred in 1998. Pollen parent: A seedling named 'A71-2' is one of our seedlings from our A-generation of plants bred in 1998.

*Growth habit.*—Upright and compact.

*Plant height.*—18–23 cm.

*Spreading area of plant.*—20–30 cm.

*Strength.*—Resistant to hot and cold weather. Plants have been exposed to temperatures ranging from 0° C.–35° C.

*Branching character.*—Freely branching and lateral branching at every node.
*Blooming period.*—From April until November: The plant displays very early flowering at 27–32 days after potting.
*Propagation.*—Vegetative stem cuttings.
*Sexuality.*—Hermaphrodite.
*Time to initiate roots.*—Approximately 10 days at temperatures of 21 degrees centigrade is needed to produce rooted cuttings.
*Root system.*—Numerous and fine, the color is N155A.
*Disease and pest susceptibility and resistance.*—There are no disease problems known to the inventor other than what affects typical *Nemesia.*

The stem:
*Diameter.*—3–4 mm.
*Length.*—8–10 cm.
*Shape.*—Quadrilateral with ridges.
*Anthocyanin pigmentation.*—Absent.
*Color of the stem.*—137B.
*Length of internode.*—20–35 mm, depending on the light where the plant is propagated.
*Pubescence.*—Glabrous.
*Length lateral branches.*—8–12 cm.

The foliage:
*Phyllotaxis.*—Opposite.
*Shape of blade.*—Ovate.
*Attachment.*—Petiolate.
*Texture.*—Upper side: Glabrous. Lower side: Glabrous.
*Venation.*—Pinnate.
*Leaf margin.*—Serrate.
*Leaf base.*—Obtuse.
*Leaf apex.*—Acute.
*Length.*—25–60 mm.
*Width.*—15–40 mm.
*Depth of incision.*—1–2 mm.
*Color.*—Upper side: 139A. Lower side: 138B.
*Petiole length.*—1–4 mm.
*Petiole surface structure.*—Glabrous.
*Petiole diameter.*—2–3 mm.
*Petiole coloration.*—Upper side: 139B. Lower side: 138A.

The bud:
*Peduncle length.*—10–30 mm, depending on season.
*Peduncle diameter.*—2–3 mm.
*Peduncle color.*—137B.
*Peduncle surface.*—Glabrous.
*Pedicel length.*—4–12 mm.
*Pedicel diameter.*—Less than 1 mm.
*Pedicel color.*—137C.
*Pedicel surface.*—Glabrous.
*Stipule length.*—1–3 mm.
*Stipule width.*—1–2 mm.
*Stipule shape.*—Lanceolate.
*Stipule color.*—Upper side: 137B. Lower side: 137C.
*Bud size.*—Diameter: 4 mm. Length: 3–5 mm.
*Bud shape.*—Globular.
*Bud color.*—155B.
*Bud surface.*—Glabrous.
*Sepals.*—Color (upper side): 137B. Color (lower side): 137B. Form: Upright. Surface: Glabrous. Number: 5, fused. Length: 1–3 mm. Width: 1–2 mm. Shape: Lanceolate. Apex: Apiculate. Base: Fused. Margin: Entire.

The flower:
*Type of inflorescence.*—Axillary raceme.
*Flower shape.*—Personate.
*Flower color.*—Upper side: 155C. Lower side: 155B.
*Palate color.*—3A in the center and 2D to the right and left sides of the center.
*Nectary* (*located on underside of palate*).—3 mm in width and 3 mm in length.
*Nectary color.*—159C.
*Throat color.*—Upper surface: 155C. Lower surface: 2D.
*Surface of upper lip.*—Upper side: Glabrous. Lower side: Glabrous.
*Surface of lower lip.*—Upper side: Glabrous. Lower side: Glabrous.
*Lip margin.*—Lower lip: Entire. Upper lip: Entire.
*Number of lips.*—2.
*Lobes.*—Upper lip: 4. Lower lip: 1.
*Lobes on upper lip fused or unfused.*—Fused.
*Upper and lower lips fused or unfused.*—Basally fused.
*Lip apex* (*upper lip*).—Each lobe has a rounded apex.
*Lip base* (*upper lip*).—Truncate.
*Lip apex* (*lower lip*).—Obcordate.
*Lip base* (*lower lip*).—Truncate.
*Upper lip color.*—Upper side: 155C. Lower side: 155B.
*Lower lip color.*—Upper side: 155C. Lower side: 155B.
*Flower dimensions.*—1.1 cm in depth, 1.6 cm in length and 1.5 cm in width at the widest part.
*Lower lip dimensions.*—0.8 cm in length and 1.2 cm in width.
*Upper lip dimensions.*—0.8 cm in length and 1.6 cm in width.
*Lobe dimensions* (*upper lip*).—0.8 cm in length and 4 mm in width.
*Flower spur dimensions.*—0.7 cm in length and 1–2 mm in diameter.
*Spur color.*—1C.
*Calyx dimensions.*—4 mm in length and 5 mm in width.
*Calyx color.*—135B.
*No. of flowers per inflorescence.*—50 to 80.
*Fragrance.*—A strong vanilla fragrance occurs.
*Bloom time of one inflorescence.*—New florets continue to open in one inflorescence over a period of 30 days.
*Lastingness of one flower.*—3 to 7 days.

Reproductive organs:
*Androecium.*—Stamens quantity: 4. Anther shape: Ovoid. Anther length: 0.3 mm. Anther width: 0.2 mm. Anther color: 2D. Pollen amount: Scarce pollen. Pollen color: 2D.
*Gynoecium.*—Pistils quantity: 1. Pistil length: 3 mm. Stigma color: 144D. Style length: 3–5 mm. Style color: 144D. Ovary color: 144D. Ovary position: Superior. Ovary shape: Oval. Ovary dimensions: 0.3 mm in width and 0.4 mm in length.

No seedset is observed.

What is claimed is:

1. A new and distinct *Nemesia* plant named 'Nemhswhi', substantially as illustrated and described herein.

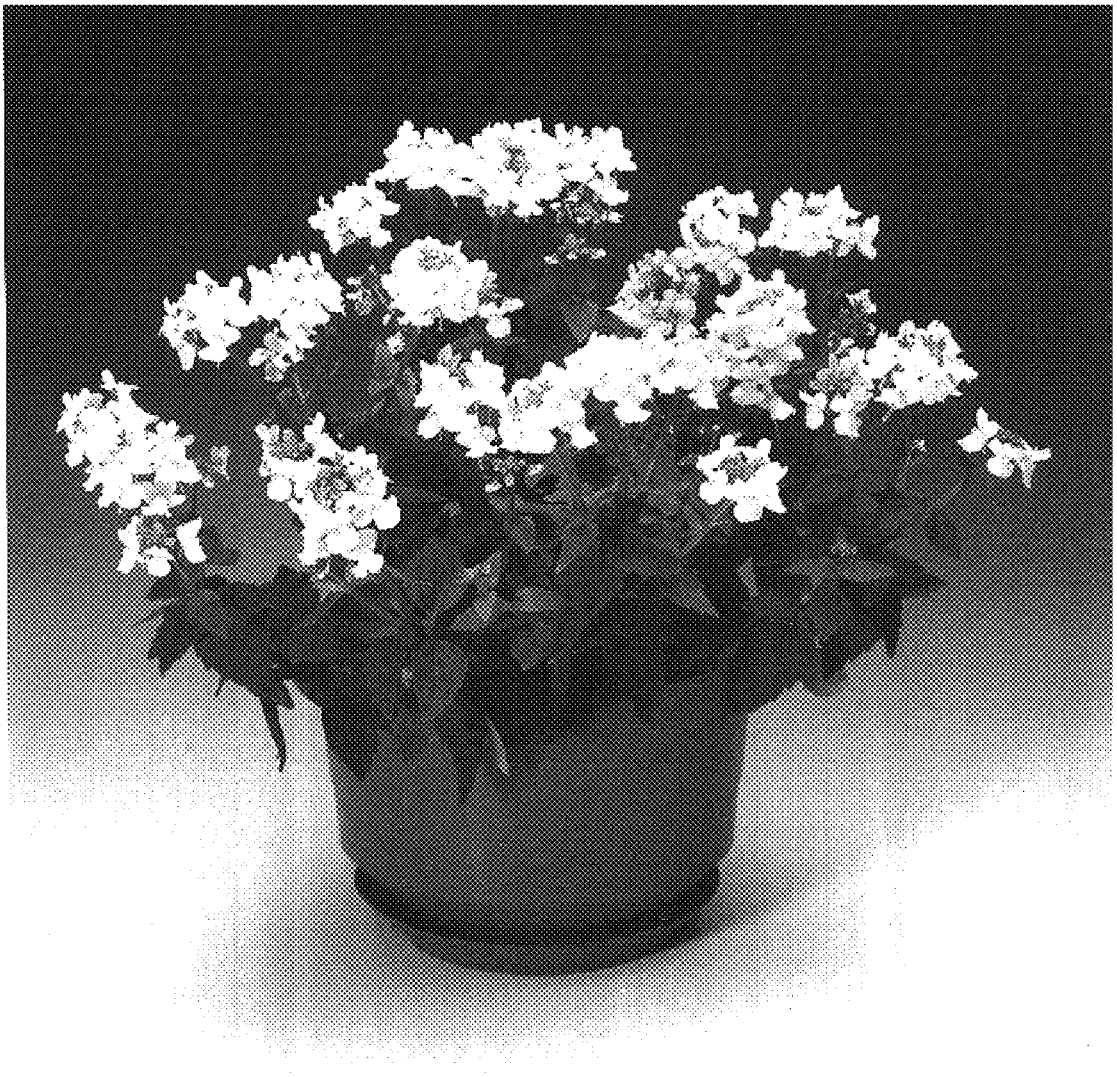

* * * * *